United States Patent [19]

Pinhack et al.

[11] Patent Number: 5,547,282
[45] Date of Patent: Aug. 20, 1996

[54] CALORIMETRIC MEASURING APPARATUS

[75] Inventors: Hubert Pinhack, Heitersheim; Jürgen Fuhrmann, Schwedt; Rolf Gegg, Freiburg, all of Germany

[73] Assignee: Ika-Analysentechnik GmbH, Heitersheim, Germany

[21] Appl. No.: 235,729

[22] Filed: Apr. 28, 1994

[30] Foreign Application Priority Data

May 3, 1993 [DE] Germany ........................ 43 14 454.3

[51] Int. Cl.$^6$ ............................................. G01N 25/22
[52] U.S. Cl. ................. 374/36; 374/33; 374/34; 422/51; 436/147
[58] Field of Search .................. 374/38, 34, 33, 374/36; 422/51; 436/147

[56] References Cited

U.S. PATENT DOCUMENTS

| 700,555 | 5/1902 | Parr | 374/38 |
|---|---|---|---|
| 3,267,728 | 8/1966 | Solomons | 374/34 |
| 3,365,944 | 1/1968 | Hoagland et al. | 374/34 |
| 3,718,437 | 2/1973 | Paloniemi | 374/33 |
| 4,208,907 | 6/1980 | Townsend et al. | 422/51 |
| 4,511,263 | 4/1985 | Prosen | 374/36 |
| 5,135,311 | 8/1992 | Alpert | 374/34 |

FOREIGN PATENT DOCUMENTS

| 3221548 | 12/1983 | Germany . | |
| 0023240 | 2/1984 | Japan | 374/34 |
| 0972360 | 11/1982 | U.S.S.R. | 374/33 |
| 2059585 | 4/1981 | United Kingdom | 374/38 |
| 2089507 | 6/1982 | United Kingdom | 374/36 |

Primary Examiner—Diego F. F. Gutierrez
Attorney, Agent, or Firm—Panitch, Schwarze, Jacobs & Nadel, P.C.

[57] ABSTRACT

A calorimetric measuring apparatus is provided with a decomposition vessel whose interior is configured as a reaction chamber and which can be tightly sealed, the decomposition vessel being removably arranged inside a jacket, and having at least one temperature sensor for measuring the temperature reached inside the decomposition vessel. Characteristic of the measuring apparatus is that the jacket has a measuring vessel which accommodates the decomposition vessel; at least some areas of the wall zone of this measuring vessel comprise a heat-conductive material; the inner walls of this measuring vessel are spaced from the outer walls of the decomposition vessel, thereby forming an interspace in which a gaseous intermediate medium is provided; and the measuring apparatus has at least a second temperature sensor for measuring the temperature change establishing itself in the heat-conductive wall zone of the measuring vessel. With the aid of the measuring apparatus calorimetric determinations of calorific value are possible with high precision and short measuring periods, whereby a comparatively large number of measurements can be carried out in one day.

8 Claims, 1 Drawing Sheet

CALORIMETRIC MEASURING APPARATUS

FIELD OF THE INVENTION

The invention relates to a calorimetric measuring apparatus with a decomposition vessel whose interior is configured as a reaction chamber and which can be tightly sealed, the decomposition vessel being removably arranged inside a jacket, and having at least one temperature sensor for measuring the temperature reached inside the decomposition vessel. Measuring apparatus of this type are used for determining the calorific value of solid and liquid product test specimens.

BACKGROUND OF THE INVENTION

In previously known calorimetric measuring apparatus functioning according to the adiabatic principle, the decomposition vessel is placed into a boiler with water. The temperature increase of the water, approximately 3° C., is measured, and is a measure of the calorific value. The measuring chamber, consisting of the decomposition vessel and the water boiler, is outwardly shielded by a water jacket that surrounds this measuring chamber on all sides; the temperature of this water jacket being adjusted to the measuring chamber temperature by heating and cooling. The high precision of this class of apparatus is achieved by great technical effort; nevertheless, penetration of the ambient temperature cannot be entirely prevented. Another drawback is the measuring time required, which can scarcely be reduced below 20 minutes per measurement.

In contrast, measuring apparatus according to the isothermal principle are distinguished by the fact that the boiler, which is filled with water and in which the decomposition vessel stands, is surrounded by a thermally stable jacket intended to prevent the transmission of energy from the outside to the inside. The energy released by the water-filled boiler to the thermally stable jacket cannot be detected. In the case of test specimens with the same energy content but with different combustion periods, this leads to different measurement results. The measuring time of these systems is no shorter than with the adiabatic principle.

The class of apparatus functioning according to the isoperibolic principle is also designed similarly to that of the isothermal measuring apparatuses. However, the decomposition vessel does not stand in a boiler, but is directly surrounded by a high-grade thermal insulator. The temperature increase of the decomposition vessel is measured by a temperature sensor and lies appreciably above the temperature increase observed with the adiabatic measurement principle or with the isothermal measurement principle. The fact that the decomposition vessel heats up considerably leads to a transfer of energy to the insulating jacket, which can neither be measured nor influenced. A heat front develops on the interior wall of the insulating vessel facing the decomposition vessel, and migrates into the insulation. The heat fronts developed during subsequent measurements overlap each other and, depending on the temperature level, energy from earlier measurements is reflected on the decomposition vessel. Distortions of the measured values are caused in this way. Devices designed according to this principle allow short measurement periods, but with limited accuracy.

SUMMARY OF THE INVENTION

The object underlying the invention is therefore to provide a calorimetric measuring apparatus of the type mentioned at the outset, which functions with high precision and short measuring periods, and can be used in a wide range of ambient temperatures.

The above object is accomplished according to the invention with the calorimetric measuring apparatus of the type mentioned at the outset, particularly wherein the jacket that surrounds the decomposition vessel is configured as a heat sink and, at least some areas thereof comprise material with good thermal conductivity and high heat capacity, wherein the inner walls and the outer walls of the heat sink are spaced from the outer walls of the decomposition vessel and the inner walls of an outer housing, thereby forming thermal insulation spaces, and wherein a temperature sensor is located in the wall zone of the heat sink and is connected with a temperature equalization device for the decomposition vessel and with a computing and/or control device.

With the measuring apparatus according to the invention, the decomposition vessel, whose walls comprise, at least in some areas, a material of good heat-conductivity, is arranged in a measuring vessel, which will be designated hereafter as a "heat sink". The space between the outer wall of the decomposition vessel and the inner wall of the heat sink is filled with air or gas. The heat sink has at least one temperature sensor for measuring the temperature which establishes itself in the heat-conductive wall zone.

In the measurement apparatus according to the invention, a temperature sensor is also provided for measuring the temperature of the decomposition vessel. The air space acting as insulating clearance between the outer wall of the decomposition vessel and the inner wall of the heat sink substantially reduces the energy transfer into the heat sink. The temperature rise of the heat sink as a result of the remaining energy transfer is measured with an additional temperature sensor. The good thermal conductivity of the corresponding wall zone of the heat sink provides for a rapid and uniform distribution of energy, so that the current measurement cannot be distorted by any heat fronts deriving from earlier measurements. By this means, the classical insulation of the decomposition vessel in conventional calorimetric measuring apparatus can be dispensed with. Since there is only a gaseous intermediate medium between the decomposition vessel and the heat sink of the apparatus according to the invention, the measurement results obtained are not distorted by a transfer of energy into an insulation layer lying between them. The insulation provided in the prior art is replaced in the measuring apparatus according to the invention by a heat sink in which the energy that is transferred into it is measured.

From the temperature change during the combustion of a product test specimen, measurable with the aid of the temperature sensors arranged in the decomposition vessel as well as in the heat sink, the calorific value of the test specimens can be determined with greater exactness. The temperature rise taking place inside the decomposition vessel during a measurement causes a transfer of energy to the heat sink by means of the air gap that serves as thermal resistance. The temperature of the heat sink is measured.

The heat sink, which warms slightly, releases energy into the surrounding air. In order to configure the energy output from the heat sink to the ambient air in a reproducible way, it is expedient if the heat sink is surrounded by a spaced jacket that keeps at least external air currents away from the heat sink.

In order to be able to convert the temperature changes at the decomposition vessel and heat sink into the corresponding calorific value of the product test specimen, it is advantageous if a computing and/or control unit is assigned to the measuring apparatus and is electrically connected with the temperature sensors. This computing and/or control unit takes into consideration the absolute start temperature and the temperature curve arising in the decomposition vessel and in the heat sink during combustion of the product test specimen. In this way, a predictive calculation of the calorimetric measurement result is possible even before the maximum temperature is reached. This makes possible short measuring periods.

In the measuring apparatus according to the invention, the decomposition vessel is removably arranged in the heat sink. Generally, a plurality of decomposition vessels is in use, whereby, for example, while one measurement is being carried out, an additional decomposition vessel can be prepared for the next measurement. For this purpose, the decomposition vessel containing the next test specimen and already filled with oxygen is placed into a temperature equalization device that is assigned to the measuring apparatus and in which the temperature of the decomposition vessel is matched to the temperature of the heat sink. Since the temperature of the heat sink is dependent on the preceding measurements and on the prior history of the measuring apparatus, it is to be considered a variable for every measurement that follows. The temperature equalization device is connected to the computing and/or control unit.

In doing this, the temperature equalization device can be assigned its own temperature sensor in the heat-conductive zone of the heat sink. In one embodiment of the measuring apparatus according to the invention, it is contemplated, for example, that two temperature sensors are arranged at the heat sink, one connected to the temperature equalization device and the other connected to the computing and/or control unit. While the one temperature sensor of the heat sink is provided for measuring the temperature establishing itself in the heat-conductive wall zone, the other temperature sensor serves for adjustment of the temperature equalization device to the respective temperature establishing itself in the heat sink at the time.

However, in order to eliminate inaccuracies that can possibly result from the use of two temperature sensors in the heat sink it is expedient if a common temperature sensor is provided, preferably disposed in an outwardly opening recess in the heat-conductive wall zone of the heat sink. In this preferred embodiment, the computing and/or control unit is thus electrically connected with only one temperature sensor arranged in the heat sink, which sensor is used both for determining the energy transferred to the heat sink during a measurement and for controlling the temperature equalization device.

The heat sink may have walls made of metal or a similar solid material, for example aluminum. It is also possible, however, for the heat sink to comprise a combination of solid and liquid materials. For example, the heat sink can be configured as a double-walled vessel wherein a heat-conductive liquid is provided between the two walls of the double wall, in which any temperature change is to be determined by means of the temperature sensor.

BRIEF DESCRIPTION OF THE DRAWINGS

The foregoing summary, as well as the following detailed description of form of implementations of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown, and the individual features can be realized independently or in combination with the other features. In the drawings:

The single FIGURE shows schematically a calorimetric measurement apparatus according to the present invention used for determining the calorific values of solid and liquid test specimens.

DETAILED DESCRIPTION OF PREFERRED EMBODIMENT

Figure 1:
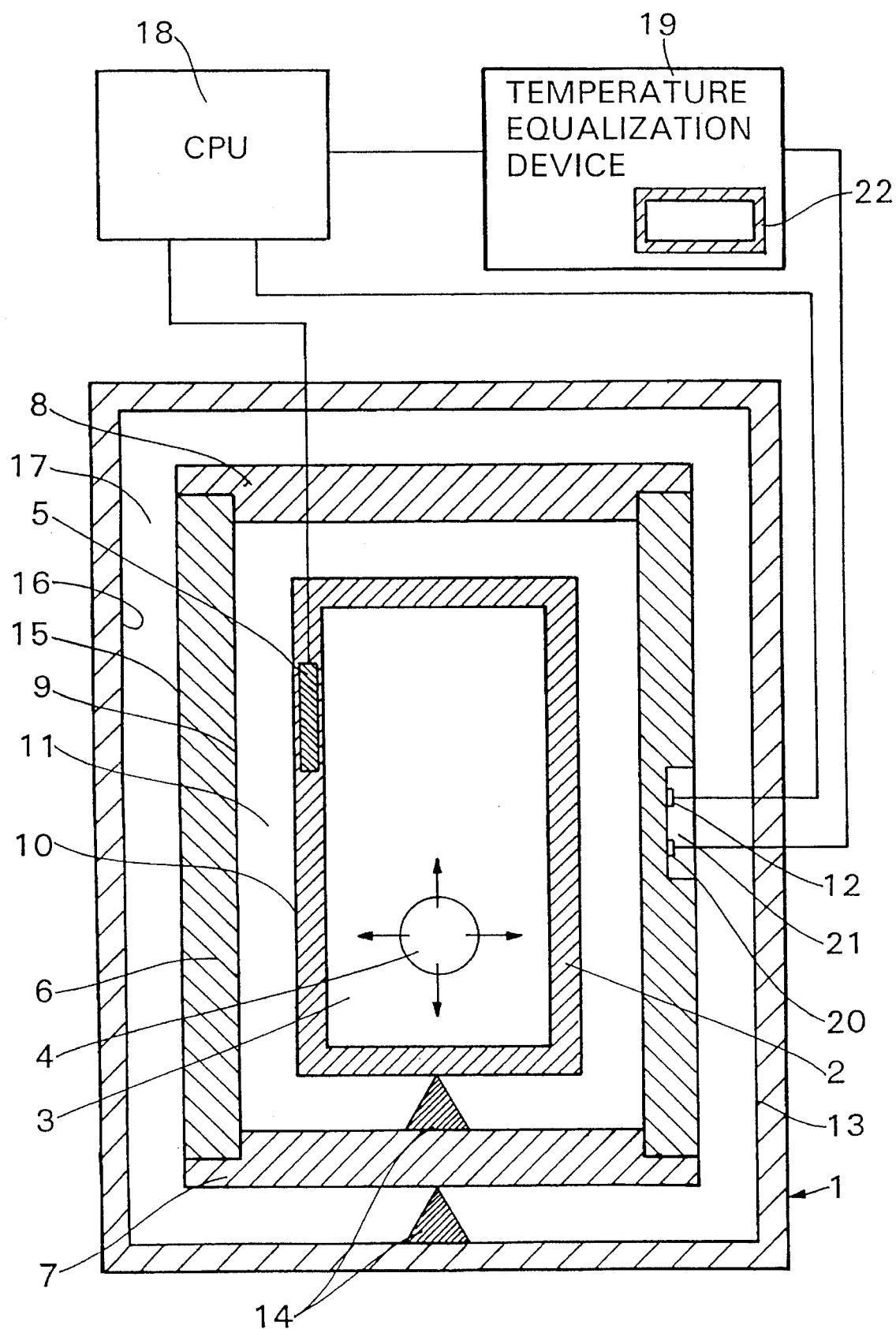

The measuring apparatus 1 has a decomposition vessel 2 which is designed as a pressure vessel and whose interior space, which can be tightly sealed, is configured as a reaction chamber 3.

To determine the calorific value of a substance, a weighed out portion of the substance is placed into the reaction chamber 3 of the decomposition vessel 2, closed up tightly, and burned under high oxygen pressure. The ignition of the test sample is carried out in a conventional manner, preferably with an ignition wire (not shown) by electrical heating of a resistance wire up to the ignition temperature of the sample 4. The temperature rise of the decomposition vessel is, inter alia, a measure of the released energy to be measured. A temperature sensor 5 is provided for measuring the temperature of the decomposition vessel 2. The decomposition vessel 2 may include more than one temperature sensor (not shown).

As shown in FIG. 1, the decomposition vessel 2 is arranged in a jacket 6. This jacket 6 will be referred to in the following as heat sink 6. The heat sink 6 has inner walls or surfaces 9 that are spaced from the outer walls or surfaces 10 of the decomposition chamber 2. The walls of the heat sink 6 are made of a material of good thermal conductivity and high heat capacity. For this purpose, the heat sink 6 here is made of thick-walled aluminum.

In order to prevent air convection during measurements in the interior of the heat sink 6, the upper and lower end faces of the heat sink are closed off by cover plates 7 and 8, so that the space inside the heat sink 6 is thermally isolated from the surrounding air space.

The temperature rise of the decomposition vessel 2 causes a slight transfer of energy to the heat sink 6 by means of the air gap 11 that serves as thermal resistance. The good heat conductivity of the material used for the heat sink 6 provides for a rapid and uniform distribution of energy into the heat sink 6. Heat fronts, which inevitably result from the finite heat-conduction rate, disperse even as the measurement takes place, and lead to a small temperature change of the heat sink 6. To measure the temperature change establishing itself in the heat-conducting wall zone of the heat sink 6, a temperature sensor 12 is provided, which can be located in an externally cut-out slot or similar recess 21.

The heat sink 6 is mounted inside a totally enclosed or closable insulating housing 13, by means of several insulation supports 14. In this way, the air gap 17 provided between the outer walls or surfaces 15 of the heat sink 6 and the inner walls or surfaces 16 of the insulating or outer housing 13 separates the heat sink 6 from the outer housing 13.

The heat sink 6 may have metal walls, but it is also possible for the heat sink to be made as, for example, a double-walled vessel made of metal or plastic. A heat-conductive liquid can be provided between the two walls of the double wall. For example, for adaptation of the heat capacity to the measuring task, this double-walled vessel is preferably filled with water, oil, or another liquid having the necessary heat content. When this is done, the temperature measurement can also be effected in the liquid if the temperature sensor 12 is immersed in the liquid.

The solid or liquid test material whose calorific value is to be determined is placed in the decomposition vessel 2 outside of the measurement apparatus 1. The decomposition vessel 2 is filled with oxygen. Then, decomposition vessel is placed in the heat sink 6. By closing the cover plate 8 of the heat sink 6 and sealing the insulating housing 13, the decomposition vessel 2 is, in practice, totally encapsulated inside this jacket. Following ignition of the test material inside the reaction chamber 3 of the decomposition vessel, the temperature rise of the decomposition vessel 2 is determined with the aid of the temperature sensor 5.

A computing and/or control unit 18 calculates the calorific value from the absolute start temperature and the temperature curves of the decomposition vessel 2 and the heat sink 6. The computing and/or control unit includes a conventional calculator design which enables all necessary control functions and measurement data readings to be automatically worked out. The calculation of the results of the measurement data and the advance calculation of the temperature curves is carried out by the selection of suitable respective software for this computing and/or control unit. The accurate measurement of the temperature curves in the decomposition vessel 2 and the heat sink 6 allows the calculation of the further temperature variation in advance, and thus the calorimetric measurement result can be determined mathematically even before the maximum temperature of the decomposition vessel is reached. Short measuring periods are thus made possible.

While a measurement with one decomposition vessel 2 is proceeding, a second or next decomposition vessel 22 can be readied for the subsequent measurement. The second decomposition vessel 22 is generally the same as the decomposition vessel 2, and is shown schematically in the drawing figure. For this purpose, the measurement apparatus 1 has associated therewith a temperature equalization device 19, particularly in the form of a cooling device which can accommodate a next decomposition vessel 22. Inside this temperature equalization device 19, the temperature of the next decomposition vessel 22 can be matched to the current temperature of the heat sink 6. To do this, the decomposition vessel 22 to be temperature equalized is placed into the temperature equalization device 19. In order that the appropriate temperature guideline of the heat sink 6 can be determined for the temperature equalization device 19, the latter is electrically connected to a further temperature sensor 20, arranged alongside the temperature sensor 12 in the recess 21 of the heat sink 6.

The temperature equalization device 19 may have its own electronic regulating device. However, an embodiment is preferred in which the temperature equalization device 19 is in a control relationship with the computing and/or control unit 18, whereby the computing and/or control unit 18 is likewise electrically connected with the temperature sensor 20 that is assigned to the temperature equalization device. Thus, by means of the control connection with the computing and/or control unit 18, the temperature equalization device 19 is monitored and the precooling started by time programming. The temperature sensor 20, arranged directly next to the temperature sensor 12 in the recess 21 of the heat sink 6, detects the temperature of the heat sink. The temperature equalization device 19 uses this temperature to temper or adjust the next decomposition vessel 22 to the temperature of the heat sink before measurement.

In order to prevent measurement differences arising from the use of two temperature sensors 12 and 20 in the heat sink 6, it may be suitable to provide in the heat sink only one temperature sensor 12 or 20, which serves both for determining the calorific value and for the temperature guideline for the temperature equalization device 19.

When the decomposition vessel 2, prepared for the measurement in the temperature equalization apparatus 19, is brought into the heat sink 6 of the measuring apparatus 1 to determine the calorific value, both vessels 2 and 6 are at approximately the same temperature. After a comparatively brief equalization period, measurement can commence. Although the temperature of the heat sink 6 is a variable, measurement commences at accurately determinable initial conditions.

The measuring apparatus 1 is distinguished by good reproducibility of the measured calorific values, even with sharply fluctuating ambient temperatures. Despite comparatively modest use of insulation materials, calorific value determinations can be realized in the measurement apparatus 1 with high precision and short measurement periods, <5 minutes. At the same time, comparatively large temperature changes in the decomposition vessel 2 are permissible during the determination of the calorific value.

To summarize, the following can be stated: The invention relates to a calorimetric measuring apparatus with a decomposition vessel whose interior is configured as a reaction chamber and which can be tightly sealed, the decomposition vessel being removably arranged in a jacket and having at least one temperature sensor for measuring the temperature reached inside the decomposition vessel. It is characteristic of the measuring apparatus according to the invention that the jacket has a measuring vessel accommodating the decomposition vessel, that at least some areas of the wall of the measuring vessel consist of a heat-conductive material, that the inner walls of this measuring vessel are spaced from the outer walls of the decomposition vessel, thereby forming an interspace in which a gaseous intermediate medium is provided, and that the measuring apparatus has at least a second temperature sensor for measuring the temperature change establishing itself in the heat-conductive wall zone of the measuring vessel. With the aid of the measuring apparatus according to the invention, calorimetric determinations of calorific value are possible with high precision and short measurement periods, whereby a comparatively large number of measurements can be realized in one day.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the form of implementation as defined by the appended claims.

We claim:

1. A calorimetric measuring apparatus comprising a decomposition vessel whose interior is configured as a reaction chamber and which can be tightly sealed, said decomposition vessel (2) being removably arranged inside a jacket and having a first temperature sensor for the measurement of temperature attained inside the decomposition vessel, said jacket surrounding the decomposition vessel (2) being configured as a heat sink (6) and having at least some portions made of a material having good thermal conductivity with a high heat capacity, said heat sink (6) having inner surfaces (9) spaced from outer surfaces (10) of the decomposition vessel (2) thereby forming a first thermal insulation space (11), an outer housing (13) which surrounds the heat sink (6) having inner surfaces (16) spaced from outer surfaces (15) of said heat sink, thereby forming a second thermal insulation space (17), and a temperature equalization device (19) adapted for receiving a second decomposition vessel 22, said device (19) being connected to a computing and control unit (18) and being connected to a temperature sensing means located at a wall zone of said heat sink for determining the temperature of the heat sink (6), the first temperature sensor and the temperature sensing means also being connected to the computing and control unit (18).

2. A measuring apparatus according to claim 1, wherein the temperature equalization device (19) is adapted to match a temperature of the second decomposition vessel (2) to a temperature of the heat sink (6) prior to a measurement, said temperature equalization device (19) being adapted to temporarily receive the second decomposition vessel (2) and being connected in a control relationship with the computing and control unit (18).

3. A measuring apparatus according to claim 2, wherein the temperature sensing means comprises second and third temperature sensors located at the heat sink (6), one of said sensors (20) being connected with the temperature equalization device (19), and the other of said sensors (12) being connected with the computing and control unit (18).

4. A measuring apparatus according to claim 2, wherein the heat sink (6) comprises a combination of solid and liquid materials.

5. A measuring apparatus according to claim 1, wherein the temperature sensing means comprises second and third temperature sensors located at the heat sink (6), one of said sensors (20) being connected with the temperature equalization device (19), and the other of said sensors (12) being connected with the computing and control unit (18).

6. A measuring apparatus according to claim 5, wherein the heat sink (6) comprises a combination of solid and liquid materials.

7. A measuring apparatus according to claim 1, wherein the heat sink (6) comprises a combination of solid and liquid materials.

8. A measuring apparatus according to claim 1 wherein the temperature sensing means comprises a second temperature sensor (12).

* * * * *